(12) United States Patent
Marano et al.

(10) Patent No.: US 6,379,658 B1
(45) Date of Patent: Apr. 30, 2002

(54) HUMAN SWEAT MALODOR COUNTERACTANT COMPOSITION AND PROCESS FOR USING SAME

(75) Inventors: Francisco Antonio Marano, Sao Paulo (BR); Lisa T. Schreck, Tinton Falls; Mary E. Gordon, Belford, both of NJ (US); Jan Tijmen Van Elst, Bilthoven (NL); Kathleen Flannelly, Hazlet; Charles E. J. Beck, Summit, both of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 34 days.

(21) Appl. No.: 09/602,269

(22) Filed: Jun. 23, 2000

Related U.S. Application Data

(60) Provisional application No. 60/172,997, filed on Dec. 21, 1999.

(51) Int. Cl.[7] ............... A61L 9/01; A61K 7/32; A61K 7/46
(52) U.S. Cl. ............ 424/65; 424/76.1; 424/76.2; 424/76.8; 424/725; 512/1; 512/5; 510/130; 422/5
(58) Field of Search .............. 424/65, 76.1, 76.2, 424/76.8, 725; 512/5, 1; 510/130; 422/5

(56) References Cited

U.S. PATENT DOCUMENTS

| | | | | |
|---|---|---|---|---|
| 4,304,679 A | * | 12/1981 | Hooper et al. | |
| 4,515,705 A | * | 5/1985 | Moeddel | |
| 4,840,792 A | * | 6/1989 | Joulain et al. | |
| 5,354,737 A | | 10/1994 | Barr et al. | 512/17 |
| 5,380,707 A | | 1/1995 | Barr et al. | 512/17 |
| 5,614,484 A | * | 3/1997 | Panandiker | |
| 5,652,206 A | * | 7/1997 | Bacon et al. | |
| 5,683,979 A | * | 11/1997 | Schreck et al. | |
| 5,919,440 A | * | 7/1999 | Kaiser et al. | |

FOREIGN PATENT DOCUMENTS

| | | | |
|---|---|---|---|
| EP | 404470 | 12/1990 | A61K/7/46 |
| EP | 780132 | 6/1997 | A61L/9/01 |

OTHER PUBLICATIONS

Chemical Abstract, Pola Chem. Ind. Inc., Nov. 10, 1993, Pokk, Japan.*
Chemical Abstract, Pola Chem. Ind. Inc. Oct. 4, 1993, Pokk, Japan.*
Chemical Abstract, Toppan Printing Co. Ltd., Sep. 24, 1993, Topp, Japan.*

* cited by examiner

Primary Examiner—Mark Kopec
Assistant Examiner—Gregory E. Webb
(74) Attorney, Agent, or Firm—Joseph F. Leightner

(57) ABSTRACT

Described is a process and compositions for counteracting human sweat malodor. The compositions containing at least 10 weight percent of either 3,7-dimethyl-2,6-nonadienenitrile or 3,7-dimethyl-2,6-octadienenitrile. Additional ingredients may be added including napthyl methyl ether, methyl beta-naphthyl ketone, benzyl acetone, methanoinden propionates, methyl ionone, tetramethylnaphthofuran, ethylene glycol cyclic ester of dodecanedioic acid, 1-cyclohexadecen-6-one, 1-cycliheptadecen-10-one, and corn mint oil. These compositions are applied to either fabric or a defined surface area of the human epidermis.

12 Claims, 2 Drawing Sheets

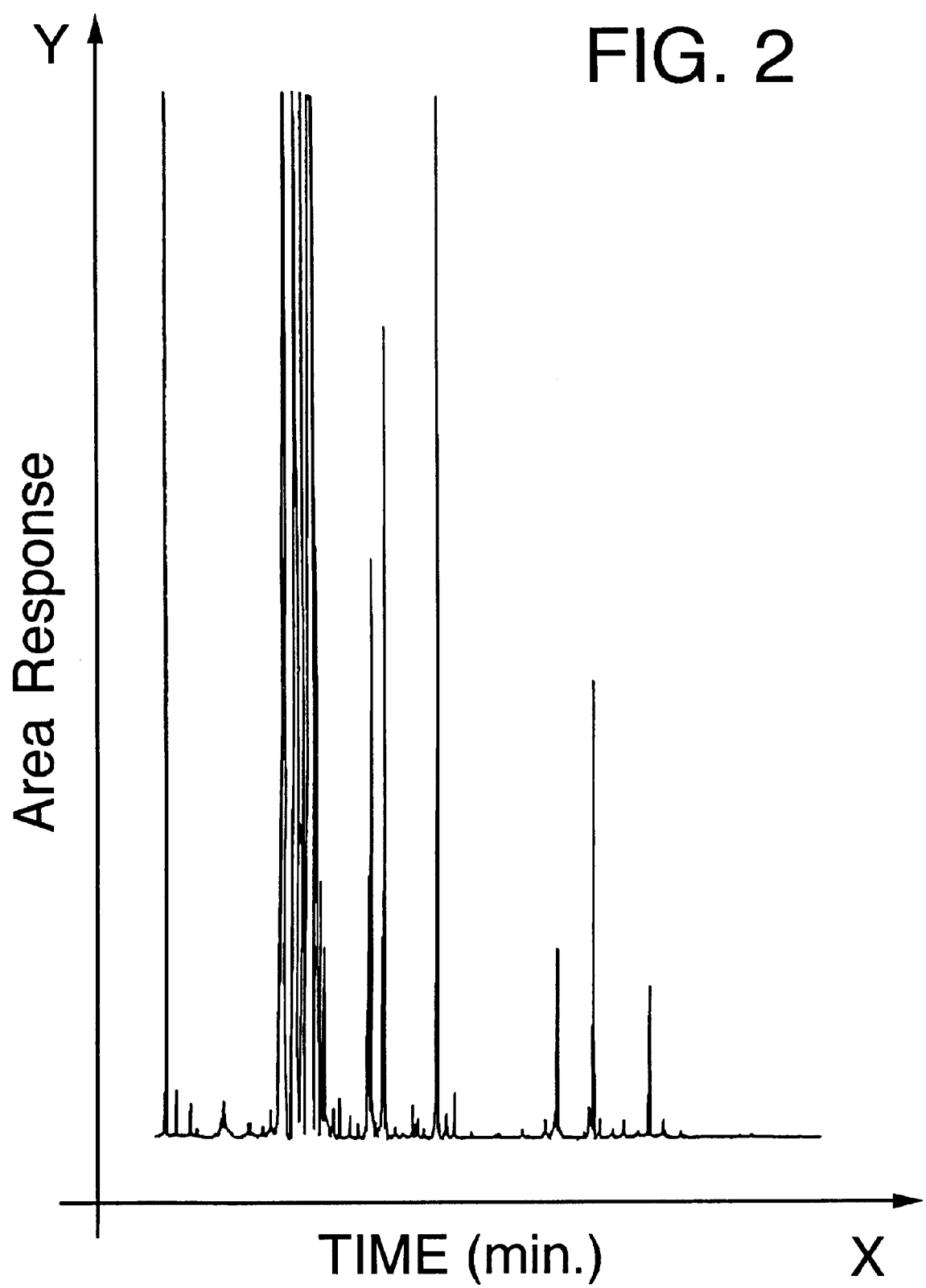

HUMAN SWEAT MALODOR COUNTERACTANT COMPOSITION AND PROCESS FOR USING SAME

RELATED COPENDING APPLICATIONS

This application is a Continuation-in-Part of Provisional Specification, Serial No. 60/172,997 filed on Dec. 21, 1999, entitled "HUMAN SWEAT MALODOR COUNTERACTANT COMPOSITION AND PROCESS FOR USING SAME." Benefit of said specification, Serial No. 60/172,997 is hereby claimed under 35 U.S.C. §119(e).

BACKGROUND OF THE INVENTION

Our invention covers technology for the creation and quantitative performance testing of substances useful as fragrance ingredients and combinations of such substances that have human sweat malodor neutralizing capacity.

The prior art contains a number of attempts at malodor coverage. The malodor coverage achieved by our invention is unobvious, unexpected and advantageous over the prior art which is set forth below.

Thus, Bair, et al, I, U.S. Pat. No. 5,354,737 issued on Oct. 11, 1994 discloses a fragrance composition said to have enhanced efficacy for masking malodor for extended periods of time, the fragrance composition containing fragrance materials that provide a topnote and/or a middle note and/or a bottom note and also containing more than 28% and up to 95% by weight of the total weight of the composition of acetyl hexamethyl tetralin. Barr, et al, I states that the fragrance composition can be incorporated in deodorant compositions to be applied to a person's skin, e.g., in axillary regions, to combat body malodor including malodor arising in axillary regions. A similar disclosure is set forth in U.S. Pat. No. 5,380,707 issued on Jan. 10, 1995 (Barr, et al, II).

Pola Chem Industries, Japan Published Application No. JP 7133490 discloses a long-lasting deodorant with malodor masking effect comprising a perfume composition containing, for example, carvone, pulegone, menthol, menthone, cineole, camphor and methyl salicylate and is abstracted in DERWENT CHEMICAL PATENTS INDEX ALERTING ABSTRACTS BULLETIN, COUNTRY ORDER, Week 9530, issued Aug. 25, 1995.

Pola Chem Industries Inc., Japanese Published Application No. JP 103964, covering selection of masking perfume based on theorization of masking by representing odorant for masking and similar odorant in making perfume separately as vectors and selective perfume(s) as indexes is abstracted.

Toppan Printing Company Limited, Japanese Published Application No. JP 7136239, discloses a deodorant containing benzoquinone derivatives in ultra small amounts for deodorizing malodors such as mercaptans and is abstracted in DERWENT CHEMICAL PATENTS INDEX ALERTING ABSTRACTS BULLETIN, COUNTRY ORDER, Week 9530, issued Aug. 25, 1995.

Joulain, et al, U.S. Pat. No. 4,840,792 issued on Jun. 20, 1989, entitled "AGENT NEUTRALIZING BAD SMELLS FROM EXCRETIONS AND EXCREMENTS OF ANIMALS", discloses and claims "a method for neutralizing disagreeable odors from animal excretions and excrement, comprising the steps of applying to a surface having a significant odor from animal excretions or excrement an agent including a compound selected from the group consisting of $C_{10}$ to $C_{12}$ aliphatic alcohols, $C_{10}$ to $C_{13}$ aldehydes, $C_{13}$ to $C_{18}$ aliphatic ketones, aromatic ketones having a musk odor and up to 18 carbon atoms, $C_8$ to $C_{15}$ aliphatic esters, methyl anthranilate, methyl N-methylanthranilate, p-cresyl phenylacetate, amyl salicylate, coumarin, dihydrocoumarin, gammadecalactone, odecalactone, undecalactone, eugenol, isoeugenol diphenyl oxide, the methyl and ethyl others of naphthol, GALAXOLIDE®, indole and its reaction products with hydroxycitronella, tridecene-2-nitrile, and 2-(2'-methyl-pent-2'enyl)-5-methyl pyridine, in an amount effective to neutralize disagreeable odors from said excretions or excrement, said agent having a vapor tension of less than or equal to 4 Pa at 25° C."

Kaiser, et al, U.S. Pat. No. 5,919,440 issued on Jul. 6, 1999 discloses personal care compositions comprising (a) from about 0.1% up to about 99.85% by weight of a malodor-producing liquid carrier and/or polymer and (b) an odor-masking base comprising 15–75% of an ionone perfume and 5–65% of a musk perfume.

Schreck, et al, U.S. Pat. No. 5,683,979 issued on Nov. 4, 1997 discloses a process for counteracting various malodors using as a maskant composition 20–60% of a musk perfumant, 1–20% of a mint substance, e.g., corn mint oil, and 30–70% of a citrus perfumant, e.g., citral.

Hooper, et al, U.S. Pat. No. 4,304,679 issued on Dec. 8, 1981 discloses a. deodorant detergent product comprising a non-soap detergent active compound and a deodorant composition which may contain three or four members of the following classes of compounds:

(i) phenolic substances;
(ii) essential oils;
(iii) aldehydes and ketones;
(iv) polycyclic compounds;
(v) esters; and
(vi) alcohols.

Nothing in the prior art however, discloses the unobvious, unexpected and advantageous human sweat malodor coverage results that we have achieved as a result of the use of the formation defined according to the claims appended hereto.

BRIEF DESCRIPTION OF THE DRAWINGS

FIG. 2 is another GLC profile of the corn mint oil used in a preferred embodiment of our invention (conditions: 50 meter OV-1, dual fused silica system programmed from 70–220° C. at 4° C. per minute).

THE INVENTION

Figure 1:
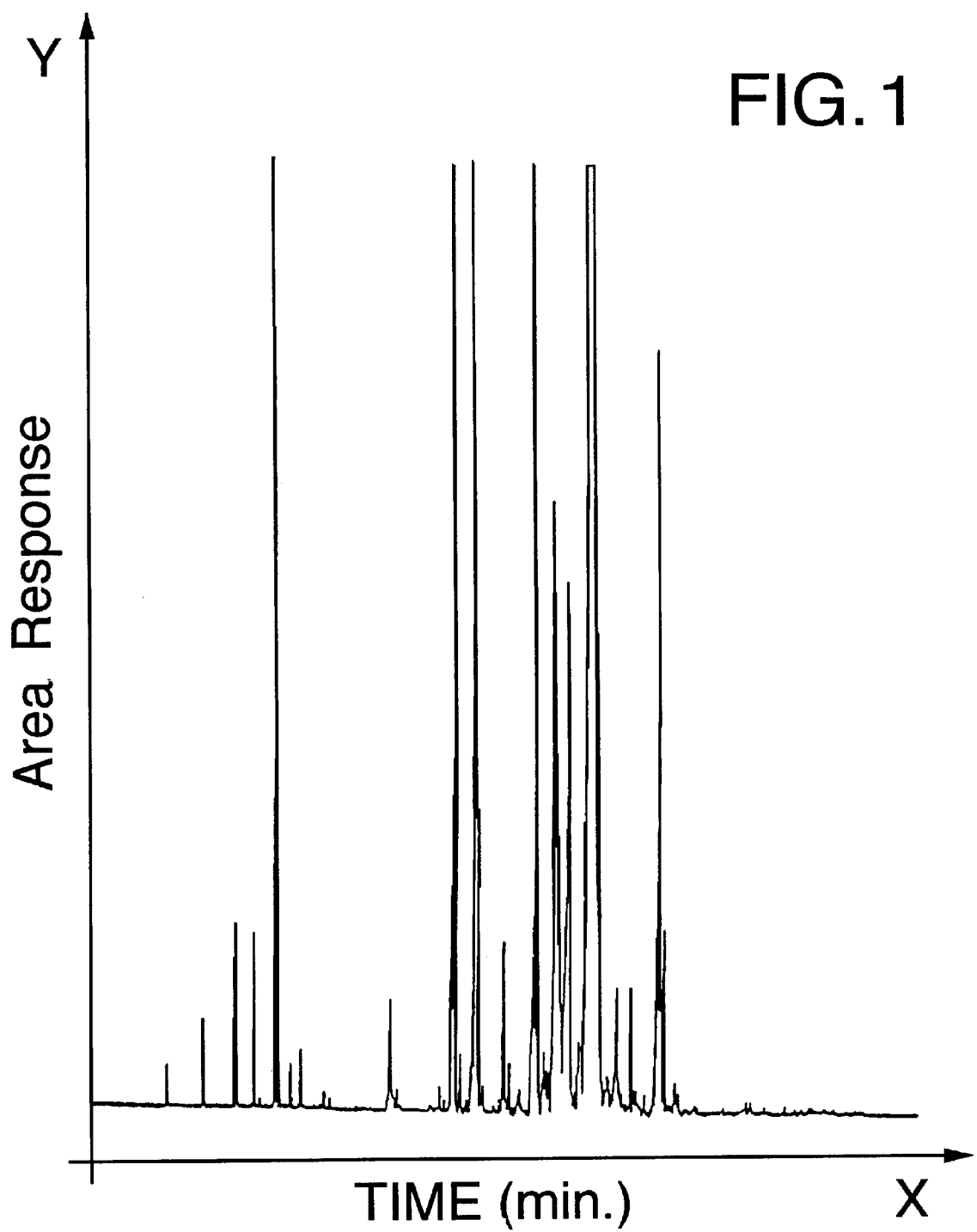
FIG. 1 is a GLC profile for the corn mint oil used in a preferred embodiment of our invention (conditions: 15 meter CARBOWAX® 20M column programmed from 70–220° C. at 4° C. per minute).

Our invention is directed to a highly substantive human sweat malodor counteractant composition and process of using same.

The malodor maskant composition of our invention contains:

(a) from about 0 weight percent up to about 10 weight percent of ,β-naphthyl methyl ether;

(b) from about 0 weight percent up to about 6 weight percent of methyl β-naphthyl ketone;

(c) from about 0 weight percent up to about 40 weight percent of benzyl acetone;

(d) from about 0 weight percent up to about 35 weight percent of a mixture of hexahydro4,7-methanoinden- 5-yl propionate and hexahydro-4,7-methanoinden-6-yl propionate (hereinafter also termed: CYCLAPROP™ (trademark of International Flavors & Fragrances Inc., New York, N.Y.));

(e) from about 0 weight percent up to about 20 weight percent of γ-methyl ionone [4-(2,6,6-trimethyl-2-cyclohexen-1-yl)-3-methyl-3-buten-2-one];

(f) from about 10 weight percent up to about 100% by weight of 3,7-dimethyl-2,6-nonadien-1-nitrile (hereinafter termed CITRALVA®, registered trademark of International Flavors & Fragrances Inc.);

(g) from about 0 up to about 50 weight percent of dodecahydro-3a,6,6,9a-tetramethylnaphtho(2,1-b)furan having the structure:

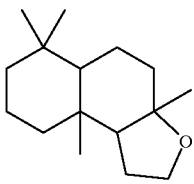

(hereinafter also termed AMBERIFF™ (trademark of International Flavors & Fragrances Inc.);

(h) from 0 up to about 50 weight percent of the ethylene glycol cyclic ester of n-docecanedioic acid having the structure:

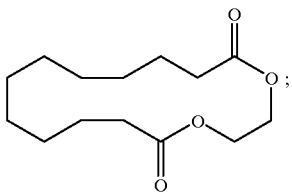

(i) from 0 up to about 10% by weight of 1-cyclohexadecen-6-one having the structure:

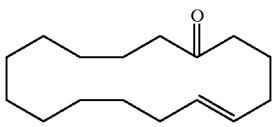

and/or 1-cycloheptadecene-10-one having the structure:

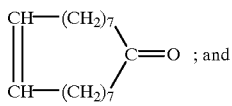

(j) from 0 up to about 35% by weight of corn mint oil defined according to the GLC profiles of one of FIGS. 1 or 2.

The following subcombinations covered by the aforementioned composition are Preferred subcombinations of our invention:

(i) (a) from 5 up to 10 weight percent of β-naphthyl methyl ether;
(b) from 3 up to 6 weight percent of β-naphthyl methyl ketone;
(c) from 20 up to 40 weight percent of benzyl acetone;
(d) from 5 up to 20 weight percent of γ-methyl ionone;
(e) from 15 up to 35 weight percent of a mixture of hexalhydro-4,7-methanoinden-5-yl propionate and hexahydro-4,7-methanoinden-6-yl propionate (in a weight ratio of 50:50); and
(f) from 10 up to 40 weight percent of 3,7-dimethyl-2,6-octadien-1-nitrile;

(ii) from about 10 up to about 90% by weight of dodecahydro-3a,6,6,9a-tetramethylnaphtho(2,1-b)furan and from about 10 up to about 90% by weight of 3,7-dimethyl-2,6-octadien-1-nitrile;

(iii) (a) from 5 up to 10 weight percent of β-naphthyl methyl ether;
(b) from 3 up to 6 weight percent of β-naphthyl methyl ketone;
(c) from 20 up to 40 weight percent of benzyl acetone;
(d) from 5 up to 20 weight percent of γ-methyl ionone;
(e) from 15 up to 35 weight percent of a mixture of hexahydro-4,7-methanoinden-5-yl propionate and hexahydro-4,7-methanoinden-6-yl propionate;
(f) from 10 up to 40 weight percent of 3,7-dimethyl-2,6-octadien-1-nitrile; and
(g) from 10 up to 40 weight percent of dodecahydro-3a,6,6,9a-tetramethylnaphtho(2,1-b)furan.

(iv) from about 10 up to about 90% by weight of dodecahydro-3a,6,6,9a-tetramethylnaphtho(2,1-b)furan; from about 20 up to 40% by weight of benzyl acetone; and from about 10 up to about 50% by weight of 3,7-dimethyl-2,6-octadien-1-nitrile; and (v) (a) from about 0.5 up to about 5% by weight of dodecahydro-3a,6,6,9a-tetramethylnaphtho(2,1-b)furan;
(b) from about 20 up to about 60% by weight of 3,7-dimethyl-2,6-octadien-1-nitrile;
(c) from about 5 up, to about 30% by weight of corn mint oil defined according to the GLC profiles of one of FIGS. 1 or 2;
(d) from about 1% up to about 10% by weight of 1-cycloheptadecen-10-one having the structure:

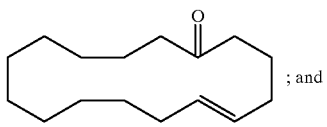
; and (e) from about 20 up to about 40% by weight of the ethylene glycol cyclic ester of n-dodecanedioic acid having the structure:

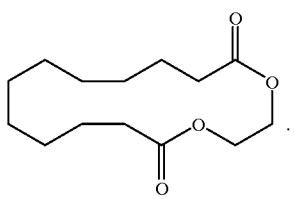

The process of our invention for neutralizing human sweat malodor emanating from A) the human epidermis and/or (B) a fabric article comprises the steps of:

(i) admixing one of the above-mentioned malodor maskant compositions with a compatible perfume formulation to form a fragranced malodor maskant composition; and then (ii) applying the resulting composition to, in the alternative:
  (a) a fabric article which evolves a human sweat malodor into the environment surrounding the fabric article; or
  (b) a defined surface area of the human epidermis (e.g., an axillary area such as underarm) which evolves into the environment proximate said surface area a human sweat malodor in a sweat malodor-reducing quantity, concentration and at a sweat malodor-reducing mass rate whereby the sweat malodor thereof is substantially totally masked.

Malodor neutralization is evaluated by placing a specified amount of malodor into an uncapped, 1 ounce wide-mouth jar. This jar is placed into an 8 ounce wide-mouth jar containing a specified amount of test material or finished fragrance. The quantities of malodor and fragrance are dependent on the specific malodor model used. The 8 ounce jar is capped and allowed to equilibrate. The panelists then rate the headspace for (1) total intensity, (2) malodor intensity and (3) overall like/dislike (hedonics). They are provided with an identified sample of malodor as a reference. Each group of samples presented to the panel contains an unidentified positive control (a fragrance material with no malodor), two unidentified negative controls (malodor with no fragrance) and up to twelve test samples (each fragrance is presented in duplicate or triplicate).

It is to be noted that evaluations are carried out by panelists who have been extensively screened for their olfactory acuity and trained in the method of evaluation (Magnitude Estimation). Panelist performance is constantly monitored and reviewed.

All samples are coded with random 5-digit numbers. Panelists are instructed to select samples from the test set and evaluate them in a random order.

The results of these experiments are expressed in terms of malodor reduction (neutralization), change in overall intensity and improvement in hedonics.

The percent malodor reduction is calculated as:

% Reduction=100×[1-(malodor intensity/total intensity)]

or shown thusly:

$$\% R_{MOL} = 100 \left\{ 1 - \frac{i_{MO}}{i_T} \right\}$$

wherein wherein $R_{MOL}$ represents malodor reduction; $i_{MO}$ is malodor intensity; and $i_T$ represents total intensity.

The positive control is normally rated as providing approximately a 95% malodor reduction; the negative control is less than 10%.

One of the important attributes of the formulations of our invention is that their efficacy should not be achieved by "overpowering" the malodor but by "blending" with it. In order to substantiate this attribute, the total intensity of the "flagrance+malodor" sample cannot be statistically more intense than the "malodor" sample alone. Also, there must be a statistically significant improvement in the perceived pleasantness (hedonics).

The technology which we have developed as exemplified below and as set forth, supra, is based upon a fragrance composition's ability to blend with a specific malodor in such a fashion as to be quantified and documented. In addition to having the appropriate aesthetic appeal these fragrances must also meet the following technical criteria:
1. significant reduction in perceived malodor when compared to appropriate control fragrances;
2. no significant increase in overall intensity when the fragrance is combined with malodor; and
3. significant increase in the level of perceived pleasantness.

The following table sets forth percents (%) human sweat malodor coverage (calculated according to the above-mentioned protocol) and substantivity for several of the human sweat malodor formulation ingredients of our invention:

| Substance | % Human Sweat Malodor Coverage | Substantivity (Time [Hours]) |
| --- | --- | --- |
| CYCLAPROP ™ | 91% reduction | 24 hours |
| Benzyl acetone | 96% reduction | 24 hours |
| CITRALVA ® | 98% reduction | 24 hours |
| β-Naphthyl methyl ether | 92% reduction | 24 hours |
| γ-Methyl ionone | 93% reduction | 24 hours |
| Methyl β-naphthalene ketone | 96% reduction | 24 hours |

The following examples are intended to indicate how the invention is to be practiced, but the invention is not to be limited thereto and is only to be limited to the claims as set forth, infra.

EXAMPLE A

FRAGRANCE A: The following fragrance was prepared:

| Ingredients | Reference Note | Parts |
| --- | --- | --- |
| Amyl Cinn Ald Coeur | 1 | 0.0157 |
| Benz Sal | 2 | 0.0714 |
| Cinn Alc | 3 | 0.0143 |
| CYCLACET ® (registered trademark of International Flavors & Fragrances Inc.) | 4 | 0.0071 |
| CYCLAPROP ™ (trademark of International Flavors & Fragrances Inc.) | 5 | 0.0071 |
| Dihydro Myrcenol | — | 0.0143 |
| Dihydro Terpineol | — | 0.0714 |
| Dipropylene Glycol | — | 0.1000 |
| GALAXOLIDE ® (registered trademark of International Flavors & Fragrances Inc.) | 6 | 0.1429 |
| Hexyl Cinn Ald | 7 | 0.1986 |
| LILIAL ® (registered trademark of (Givaudan et Cie) | 8 | 0.1486 |
| LYRAL ® (registered trademark of International Flavors & Fragrances Inc.) | 9 | 0.0229 |
| Meth Ionone γ-A | 10 | 0.0286 |
| Phen Eth Acet | 11 | 0.0286 |
| Phen Eth Alc White Extra | 12 | 0.1000 |
| TONALIDE ® (registered trademark of Tastemaker Inc.) | 13 | 0.0214 |
| TRIMOFIX "O" ® of International Flavors & Fragrances Inc.) | 14 | 0.0071 |

REFERENCE NOTES FOR FRAGRANCE A

1. Amyl cinnamic aldehyde
2. Benzyl salicylate
3. Cinnamyl alcohol
4. Hexahydro-4,7-methanoinden-5-yl acetate
5. Hexaliydro4,7-methanoinden-5-yl propionate
6. Structures on page 19, infia
7. Hexylcinnamic aldehyde
8. p-t-butyl- -methyl-dihydro cinnamic aldehyde
9. (4-hydroxy-4-methylpentyl)3-cyclohexene-1-carboxaldehyde
10. γ-Methyl ionone 11. β-Phenyl ethyl acetate
12. β-Phenyl ethyl alcohol
13. 6-Acetyl-1,2,3,4-tetrahydro-1,1,2,4,4,7-hexamethyl naphthalene
14. Methyl-2,6, 10-timethyl-2,5,9-cyclododecatrien-1-yl ketone

EXAMPLE B

The following two malodor maskant formulations are prepared and called, respectively, DEODIFF® 2000A and DEODIFF®2000B formulations (trademarks of International Flavors & Fragrances Inc.):

DEODIFF® 2000A

10% β-naphthyl methyl ether;
5% β-naphthyl methyl ketone;
30% benzyl acetone;
10% γ-methyl ionone;
20% CYCLAPROP™ (trademark of International Flavors & Fragrances Inc.); and
25% CITRALVA® (red trademark of International Flavors & Fragrances Inc.).

DEODIFF® 2000B

1% dodecahydro-3,6,6,9a-tetramethylnaphtho(2,1-b)furan (20% in isopropyl myristate);
50% CITRALVA®;
10% corn mint oil having the GLC spectra of FIGS. 1 and 2; and
35% ethylene glycol cyclic ester of n-dodecanedioic acid.

The following protocols are used for cloth substantivity, for malodor and for human sweat malodor neutralization:

CLOTH SUBSTANTIVITY

1. Sufficient 3"×4.5" polyester:cotton fabric test swatches for the complete test are prewashed in an automatic washing machine using approximately ½ cup of unperfumed detergent and subsequently dried in an automatic dryer;
2. Use levels (concentration of fragrance in product base) and dosage levels (amount of fragrance product in wash load) are established appropriately for the fragrance ingredients, finished fragrances or product category to be tested;
3. All samples are processed using a Launder-O-Meter® Model LEF (trademark of Atlas Electric Devices Company, Chicago, Ill.). A 1,200 ml container is charged with 40 grams of prewashed fabric, 750 ml of distilled water and an appropriate amount of a fragranced laundry care product. The samples are agitated with stainless steel balls on the rotor under the standard Launder-O-Meters® protocol for a period of 10 minutes for fabric softener products or 30 minutes for detergent products. The samples are then hand-squeezed to approximately 200% of their original dry weight;
4. In the case of detergent products, the treated fabric samples are rinsed in 750 ml of distilled water and agitated for 10 minutes. The test samples are again hand-squeezed to approximately 200% of their original dry weight. Samples are then hung to dry in a controlled air flow room for a period of 24 hours;
5. The dry samples are then divided into four 10-gram aliquots and placed in 6 oz. wide-mouth jars for a double-blind presentation to the trained panel of magnitude estimation judges; and
6. The odor intensities are quantitatively measured and compared to the appropriate controls and embedded targets in order to rate and rank the level of substantivity.

MALODOR NEUTRALIZING EVALUATIONS—FRAGRANCE INGREDIENTS

The following protocol has been developed to determine the level of odor neutralization:

1. A predetermined quantity of the malodor model is measured with a micropipette into an uncapped 1 oz. wide-mouth jar. This jar is subsequently placed into an 8 oz. wide-mouth jar containing a predetermined quantity of the test material. The 8 oz. jar is capped and allowed to equilibrate prior to evaluation;
2. Odor evaluations are completed by judges who have been trained in the use of Magnitude Estimation They are presented with a filly randomized array of samples, including duplicates of each test product, blanks, positive and negative controls, internal standards and/or relevant commercial targets. Each judge is also presented with an identified sample of the malodor in order to reinforce the malodor discrimination task;
3. Each of the judges rate the headspace for (a) total odor intensity, (b) malodor intensity and (c) the overall like/dislike (hedonics) of the sample; and
4. In order to meet our efficacy criteria for malodor neutralization, a fragrance or test material must reduce the perception of the unpleasant note and significantly increase the overall pleasantness of the odor without significantly increasing the overall odor intensity.

Using the aforementioned protocols, the following sweat malodor neutralization (jar method) and cloth substantivity are obtained for each of DEODIFF® 2000B and DEODIFF® 2000A and Fragrance A:

| Substance Tested | Sweat Malodor Neutralization (Jar Method) | Cloth Substantivity |
| --- | --- | --- |
| DEODIFF ® 2000B | 83 | + |
| DEODIFF ® 2000A | 82 | + |
| Fragrance A | 74 | + |

A "A" in the aforementioned table indicates substantivity of 24 hours.

CONCLUSION

The original fragrance of Example A was developed to be aesthetically appropriate for sweat malodor coverage. Although hedonically acceptable, the fragrance is less than adequate for sweat malodor neutralization.

DEODIFF® A and DEODIFF® B have unexpected, unobvious and advantageous effects in the field of human sweat malodor coverage.

What is claimed is:
1. A process for neutralizing human sweat malodor emanating from a fabric article comprising the steps of:
   (i) admixing a malodor maskant composition consisting essentially of:
      (a) from about 0 weight percent up to about 10 weight percent of β-naphthyl methyl ether;
      (b) from about 0 weight percent up to about 6 weight percent of methyl β-naphthyl ketone;

(c) from about 0 weight percent up to about 40 weight percent of benzyl acetone;

(d) from about 0 weight percent up to about 35 weight percent of a 50:50 weight:weight mixture of hexahydro-4,7-methanoinden-5-yl propionate and hexahydro-4,7-methanoinden-6-yl propionate;

(e) from about 0 weight percent up to about 20 weight percent of γ-methyl ionone;

(f) from about 10 weight percent up to about 100% by weight of 3,7-dimethyl-2,6-nonadien-1-nitrile;

(g) from 0 up to about 50 weight percent of dodecahydro-3a,6,6,9a-tetramethylnaphtho(2,1-b) furan having the structure:

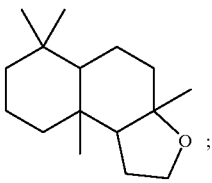

(h) from 0 up to about 50 weight percent of the ethylene glycol cyclic ester of n-dodecanedioic acid having the structure:

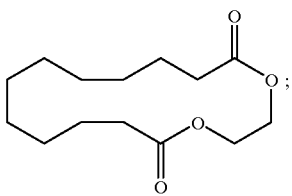

(i) from 0 up to about 10% by weight of 1-cyclohexadecen-6-one and/or 1-cycloheptadecen-10-one having the structure:

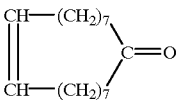

(j) from 0 up to about 35% by weight of corn mint oil defined according to the GLC profiles of one of FIGS. 1 or 2, with a compatible perfume formulation to form a fragranced malodor maskant composition; and (ii) applying the resulting composition to a fabric article which evolves into the environment surrounding said fabric article a human sweat malodor, in a sweat malodor-reducing quantity, concentration and at a sweat malodor-reducing mass rate whereby the sweat malodor thereof is substantially totally masked.

2. The process of claim 1 wherein the malodor maskant composition contains:

(a) from 5 up to 10 weight percent of β-naphthyl methyl ether;

(b) from 3 up to 6 weight percent of β-naphthyl methyl ketone;

(c) from 20 up to 40 weight percent of benzyl acetone;

(d) from S up to 20 weight percent of γ-methyl ionone;

(e) from 15 up to 35 weight percent of a 50:50 mixture of hexahydro-4,7-methanoinden-5-yl propionate and hexahydro-4,7-methanoinden-6-yl propionate; and (f) from 10 up to 40 weight percent of 3,7-dimethyl-2,6-octadien-1-nitrile.

3. The process of claim 1 wherein the malodor maskant composition contains from about 10 up to about 90% by weight of dodecahydro-3a,6,6,9a-tetramethylnaphtho(2,1-b) furan and from about 10 up to about 90% by weight of 3,7-dimethyl-2,6-octadien-1-nitrile.

4. The of claim 1 wherein the malodor maskant composition contains from about 10 up to) about 90% by weight of dodecahydro-3a,6,6,9a-tetramethylnaphtho(2,1-b)furan; from about 20 up to about 40% by weight of benzyl acetone; and from about 10 up to about 90 weight percent of 3,7-dimethyl-2,6-octadien-1-nitrile.

5. The process of claim 1 wherein the malodor maskant composition contains:

0.5–5% dodecahydro-3a,6,6,9a-tetramethylnaphtho(2,1-b)furan;

20–60% geranonitrile;

5–30% corn mint oil;

1–10% 1-cycloheptadecen-6-one; and

20–40% ethylene glycol cyclic ester of n-dodecanedioic acid.

6. A composition of matter consisting essentially of from about 10 up to about 90% by weight of dodecahydro-3a,6,6,9a-tetramethylnaphtho(2,1-b)furan and from about 10 up to about 90% by weight of 3,7-dimethyl-2,6-octadien-1-nitrile.

7. A composition of matter consisting essentially of:

(a) from 5 up to 10 weight percent of β-naphthyl methyl ether;

(b) from 3 up to 6 weight percent of β-naphthyl methyl ketone;

(c) from 20 up to 40 weight percent of benzyl acetone;

(d) from 5 up to 20 weight percent of γ-methyl ionone;

(e) from 15 up to 35 weight percent of a 50:50 mixture of hexahydro-4,7-methanoinden-5-yl propionate and hexahydro-4,7-methanoinden-6-yl propionate; and (f) from 10 up to 40 weight percent of 3,7-dimethyl-2,6-octadien-1-nitrile.

8. A process for neutralizing human sweat malodor emanating from a fabric article comprising the steps of:

(i) admixing a malodor maskant composition consisting essentially of:

(a) from 5 up to 10 weight percent of β-naphthyl methyl ether;

(b) from 3 up to 6 weight percent of methyl β-naphthyl ketone;

(c) from 20 up to 40 weight percent of benzyl acetone;

(d) from about 0 weight percent up to about 35 weight percent of a 50:50 mixture of hexahydro4,7-methanoinden-5-yl propionate and hexahydro-4, 7methanoinden-6-yl propionate;

(e) from about 0 weight percent up to about 20 weight percent of γ-methyl ionone;

(f) from 10 weight percent up to 90% by weight of 3,7-dimethyl-2,6-octadien-1-nitrile; and (g) from 0 up to about 50 weight percent of dodecahydro-3a,6,6,9a-tetramethylnaphtho(2,1-b) furan having the structure:

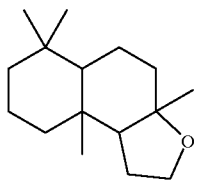

with a compatible perfume formulation to form a fragranced malodor maskant composition; and (ii) applying the resulting composition to a fabric article which evolves into the environment surrounding said fabric article a human sweat malodor, in a sweat malodor-reducing quantity, concentration and at a sweat malodor-reducing mass rate whereby the sweat malodor thereof is substantially totally masked.

9. The process of claim 8 wherein the malodor maskant composition contains:

(a) from 5 up to 10 weight percent of β-naphthyl methyl ether;

(b) from 3 up to 6 weight percent of β-naphthyl methyl ketone;

(c) from 20 up to 40 weight percent of benzyl acetone;

(d) from 5 up to 20 weight percent of γ-methyl ionone;

(e) from 15 up to 35 weight percent of a 50:50 mixture of hexahydro-4,7-methanoinden-5-yl propionate and hexahydro-4,7methanoinden-6-yl propionate;

(f) from 10 up to 40 weight percent of 3,7-dimethyl-2,6-octadien-1-nitrile; and (g) from 10 up to 40 weight percent of dodecahydro-3a,6,6,9a-tetramethylnaphtho(2,1-b)furan.

10. A composition of matter consisting essentially of from about 10 up to about 90% by weight of dodecahydro-3a,6,6,9a-tetramethylnaphtho(2,1-b)furan; from about 20 up to about 40 weight percent of benzyl acetone; and from about 10 up to about 90% by weight of 3,7-dimethyl-2,6-octadien-1-nitrile.

11. A composition of matter consisting essentially of:

(a) from 5 up to 10 weight percent of β-naphthyl methyl ether;

(b) from 3 up to 6 weight percent of β-naphthyl methyl ketone;

(c) from 20 up to 40 weight percent of benzyl acetone;

(d) from 5 up to 20 weight percent of γ-methyl ionone;

(e) from 15 up to 35 weight percent of a 50:50 mixture of hexahydro-4,7-methanoinden-5-yl propionate and hexahydro-4,7-methanoinden-6-yl propionate;

(f) from 10 up to 40 weight percent of 3,7-dimethyl-2,6-octadien-1-nitrile; and (g) from 10 up to 40 weight percent of dodecahydro-3a,6,6,9a-tetramethylnaphtho(2,1-b)furan.

12. A composition consisting essentially of:

0.5–5% dodecahydro-3a,6,6,9a-tetramethylnaphtho(2,1-b)furan;

20–60% geranonitrile;

5–30% corn mint oil;

1–10% 1-cycloheptadecen-6-one; and

20–40% ethylene glycol cyclic ester of n-dodecanedioic acid.

\* \* \* \* \*